(12) United States Patent
Davenport et al.

(10) Patent No.: US 8,439,901 B2
(45) Date of Patent: *May 14, 2013

(54) FRACTIONAL SCANNER FOR DERMATOLOGICAL TREATMENTS

(71) Applicant: Cutera, Inc., Brisbane, CA (US)

(72) Inventors: Scott A. Davenport, Half Moon Bay, CA (US); David A. Gollnick, San Francisco, CA (US)

(73) Assignee: Cutera, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/658,719

(22) Filed: Oct. 23, 2012

(65) Prior Publication Data

US 2013/0060307 A1   Mar. 7, 2013

Related U.S. Application Data

(63) Continuation of application No. 12/405,085, filed on Mar. 16, 2009.

(60) Provisional application No. 61/041,745, filed on Apr. 2, 2008.

(51) Int. Cl.
*A61B 18/18* (2006.01)

(52) U.S. Cl.
USPC .................. 606/9; 606/11; 606/13; 607/89

(58) Field of Classification Search ........... None
See application file for complete search history.

(56) References Cited

U.S. PATENT DOCUMENTS

| | | | |
|---|---|---|---|
| 4,233,493 A | 11/1980 | Nath | |
| 4,939,739 A | 7/1990 | Hobart et al. | |
| 5,336,217 A | 8/1994 | Buys et al. | |
| 5,339,347 A | 8/1994 | Slatkin et al. | |
| 5,743,870 A | 4/1998 | Edwards | |
| 5,743,902 A | 4/1998 | Trost | |
| 6,059,820 A | 5/2000 | Baronov | |
| 6,090,102 A | 7/2000 | Telfair et al. | |
| 6,517,532 B1 | 2/2003 | Altshuler et al. | |
| 6,585,725 B1 | 7/2003 | Mukai | |
| 6,723,090 B2 | 4/2004 | Altshuler et al. | |
| 6,997,923 B2 | 2/2006 | Anderson et al. | |
| 7,090,670 B2 | 8/2006 | Sink | |
| 7,331,953 B2 | 2/2008 | Manstein et al. | |

(Continued)

OTHER PUBLICATIONS

Apfelberg et al., "Dot or Pointillistic Method for Improvement in Results of Hypertrophic Scarring in the Argon Laser Treatment of Portwine Hemangiomas", Lasers in Surgery and Medicine, vol. 6, 1987, pp. 552-558.

(Continued)

*Primary Examiner* — Bill Thomson
*Assistant Examiner* — Lynsey Crandall
(74) *Attorney, Agent, or Firm* — Morrison & Foerster LLP

(57) ABSTRACT

A dermatological treatment device is disclosed for generating a matrix of two dimensional treatment spots on the tissue. A handpiece carries a laser which generates a beam of laser pulses. The pulses are focused onto the tissue with a lens system. A diffractive element is positioned between the laser and the lens system for splitting the laser beam into a plurality of sub-beams. A scanner translates the beam over the diffractive element to generate the two dimensional spot pattern. The laser has a semi-monolithic resonator design with one integral end minor defining the output coupler and a second, independent mirror for adjustment.

11 Claims, 6 Drawing Sheets

U.S. PATENT DOCUMENTS

| | | |
|---|---|---|
| 7,372,606 B2 | 5/2008 | Broome et al. |
| 7,480,086 B2 | 1/2009 | DeBenedictis et al. |
| 7,486,426 B2 | 2/2009 | Broome et al. |
| 7,566,173 B2 | 7/2009 | Auld et al. |
| 2003/0216719 A1 | 11/2003 | Debenedictis et al. |
| 2005/0049582 A1 | 3/2005 | DeBenedictis et al. |
| 2005/0171581 A1 | 8/2005 | Connors et al. |
| 2005/0215987 A1 | 9/2005 | Slatkine |
| 2006/0155266 A1 | 7/2006 | Manstein et al. |
| 2006/0276778 A1 | 12/2006 | Sink |
| 2007/0179481 A1 | 8/2007 | Frangineas et al. |
| 2007/0239079 A1 | 10/2007 | Manstein et al. |
| 2007/0265604 A1 | 11/2007 | Davenport et al. |
| 2007/0265606 A1 | 11/2007 | DeBenedictis et al. |
| 2008/0058782 A1 | 3/2008 | Frangineas et al. |
| 2008/0068694 A1 | 3/2008 | DeBenedictis et al. |

OTHER PUBLICATIONS

Fitzpatrick, R. E., "Laser Hair Transplantation. Tissue Effects of Laser Parameters", Dermatologic Surgery, vol. 21, 1995, pp. 1042-1046.

Grevelink, J. M., "Laser Hair Transplantation", Dermatologic Clinics, vol. 15, No. 3, Jul. 1997, pp. 479-486.

Ho et al., "Mini-Slit Graft Hair Transplantation Using the Ultrapulse Carbon Dioxide Laser Handpiece", Dermatologic Surgery, vol. 21, 1995, pp. 1056-1059.

Mordon et al., "Rationale for Automatic Scanners in Laser Treatment of Port Wine Stains", Lasers in Surgery and Medicine, vol. 13, 1993, pp. 113-123.

Non Final Office Action received for U.S. Appl. No. 12/405,085, mailed on Oct. 28, 2011, 10 pages.

Rubach et al., "Histological and Clinical Evaluation of Facial Resurfacing Using a Carbon Dioxide Laser With the Computer Pattern Generator", Archives of Orolaryngology—Head & Neck Surgery, vol. 123, Sep. 1997, pp. 929-934.

Unger, W. P., "Laser Hair Transplantation II", Dermatologic Surgery, vol. 21, 1995, pp. 759-765.

Unger, W. P., "Laser Hair Transplantation III. Computer-Assisted Laser Transplantating", Dermatologic Surgery, vol. 21, 1995, pp. 1047-1055.

Unger, W. P., "Laser Hair Transplantation", Letter to the Editor and Response, Dermatologic Surgery, vol. 21, 1995, pp. 186-187.

Unger et al., "Laser Hair Transplantation", The Journal of Dermatologic Surgery and Oncology, vol. 20, 1994, pp. 515-521.

Unger, W. P., "What's New in Hair Replacement Surgery", Dermatologic Clinics, vol. 14, No. 4, Oct. 1996, pp. 783-802.

Final Office Action received for U.S. Appl. No. 12/405,085, mailed on May 11, 2012, 10 pages.

Notice of Allowance received for U.S. Appl. No. 12/405,085, mailed on Aug. 29, 2012, 10 pages.

Non Final Office Action received for U.S. Appl. No. 13/272,010, mailed on May 8, 2012, 14 pages.

Notice of Allowance received for U.S. Appl. No. 13/272,010, mailed on Aug. 10, 2012, 8 pages.

FRACTIONAL SCANNER FOR DERMATOLOGICAL TREATMENTS

CROSS REFERENCE TO RELATED APPLICATIONS

This application is a Continuation of U.S. patent application Ser. No. 12/405,085, with a filing date of Mar. 16, 2009, which claims priority to U.S. Provisional Application Ser. No. 61/041,745 filed Apr. 2, 2008, the disclosures of which are herein incorporated by reference in their entirety.

TECHNICAL FIELD OF THE INVENTION

The present invention relates generally to the field of dermatological treatment, and more specifically to the field of dermatological treatment lasers.

BACKGROUND

A dermatological treatment laser incorporating a laser resonator into a handpiece is disclosed in U.S. Publication No. US 2007/0265604, which is commonly owned with the present application and is incorporated herein by reference. The resonator includes an Er:YSGG or Cr,Er:YSGG gain medium, which has a primary output at 2.79 μm. The handpiece includes two stepper motors that scan the laser output in two axes. In one exemplary method, the handpiece is held in a fixed position while a pattern of 5 mm treatment spots is formed on the skin by stepping the treatment beam in X and Y directions.

For certain applications such as treatment of deep wrinkles, it may be beneficial to treat the skin using a matrix of much smaller diameter (e.g. approximately 200-400μ) non-overlapping spots. With the reduced spot size, a much larger number of spots is needed for a given treatment area. The present application discloses a laser handpiece suitable for generating the large number of spots more quickly than if each spot was generated individually.

DETAILED DESCRIPTION

Figure 1:
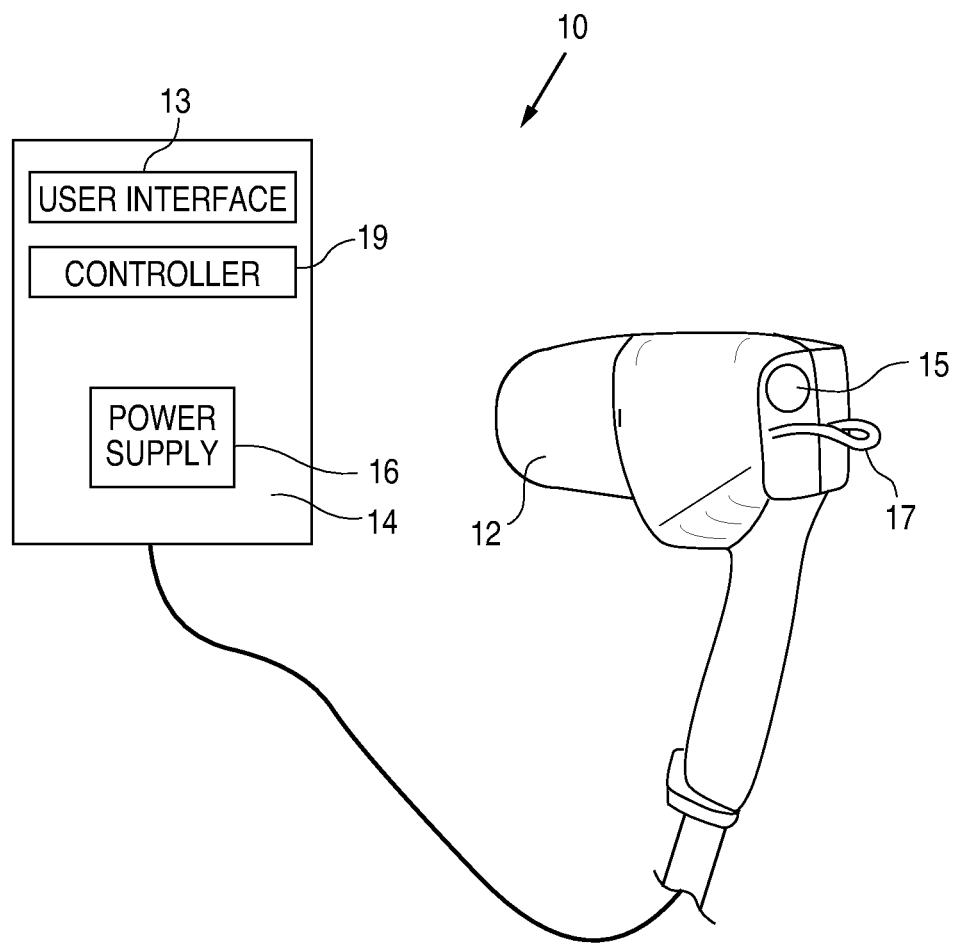
FIG. 1 is a perspective view of a handpiece housing a fractionalized laser scanner.

Referring to FIG. 1, a treatment apparatus 10 includes a handpiece 12 coupled to a treatment console 14 which includes a user interface 13, a power supply 16 and a controller 19. Power supply 16 may be a high voltage power supply of the type provided by Cutera, Inc. (Brisbane Calif.) in consoles for use with its laser product lines, and in particular the power supply used with the PEARL™ laser.

The exterior of handpiece 12 includes a protective window 15 through which treatment energy exits the handpiece. A distance guide 17 sets the distance between the handpiece 12 and the target treatment site. During use, the distance guide is placed in direct contact with the patient's skin.

Figure 2A:
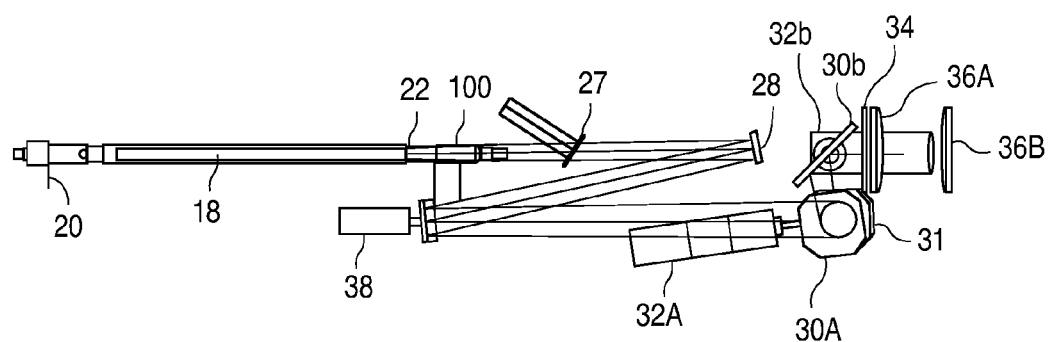
FIG. 2A is a top plan view schematically illustrating the components of the handpiece of FIG. 1.
Figure 2B:
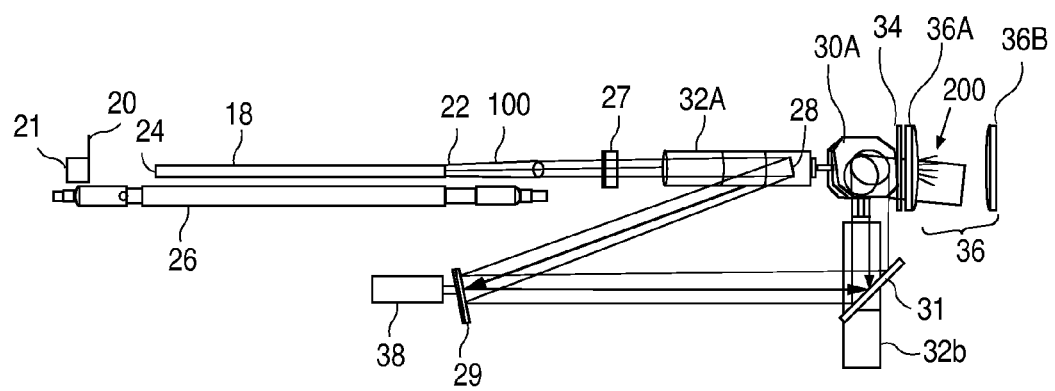
FIG. 2B is a side elevation view schematically illustrating the components of the handpiece of FIG. 1.

Features housed within the handpiece 12 are shown in FIGS. 2A and 2B. These features include a semi-monolithic laser resonator comprising a laser rod 18 and a planar minor 20. The laser rod 18 is preferably a Er:YSGG or a Cr,Er:YSGG rod. This gain medium has a primary output at 2.79 μm. In one embodiment, rod 18 has a length of 86 mm and a diameter of 3 mm, and the length of the resonator is 106 mm.

As best shown in FIG. 2B, laser rod 18 includes first and second planar ends. First end 22, which serves as the output coupler, includes a polished surface coated with a partially transmissive coating. Second end 24, which is positioned in alignment with the minor 20, has an anti-reflective coating. Mirror 20 is a planar mirror aligned with the second end 24 to permit light to circulate between the minor 20 and the first end 22. Minor 20 is supported in a mount 21 which permits the tilt angle of the mirror to be adjusted during assembly to facilitate alignment with the resonator axis.

This semi-monolithic resonator design, with the output coupler 22 formed on the gain rod 18 and the second minor 20 being spaced from the end of the rod was developed to improve the M$^2$ output of the laser to increase the depth of focus of the beam. More specifically, in the laser resonator used in the assignee's Pearl laser system was fully monolithic wherein both ends of the gain rod were coated for reflection. In such a fully monolithic laser resonator, the ends of the rod were curved for stability purposes. Curved minors tend to produce a higher M$^2$ output with a short depth of focus. This short depth of focus was not a problem with the Pearl system because of its large spot size at the tissue.

The semi-monolithic design reduces the M2 because it uses two flat mirrors and is longer than the prior art resonator. By mounting minor 21 on a tiltable support, alignment is facilitated. The increased depth of focus is very useful for maintaining the desired spot size on the tissue for multiple small spots.

The rod 18 is side-pumped flashlamp 26 to generate a pulsed output. A portion of the beam 100 exiting the laser resonator may be diverted to a photodetector (not shown) by a beam splitter 27 for use in monitoring output power.

Mirrors 28, 29 and 31 are positioned to direct the output beam from the laser to a pair of scanning mirrors 30a, 30b. Each of the scanning mirrors 30a, 30b is coupled to a corresponding stepper motor 32a, 32b. Stepper motors 32a, 32b are simultaneously or independently operable to scan the output beam 100 in X- and/or Y-directions across a diffractive element 34.

Figure 3A:
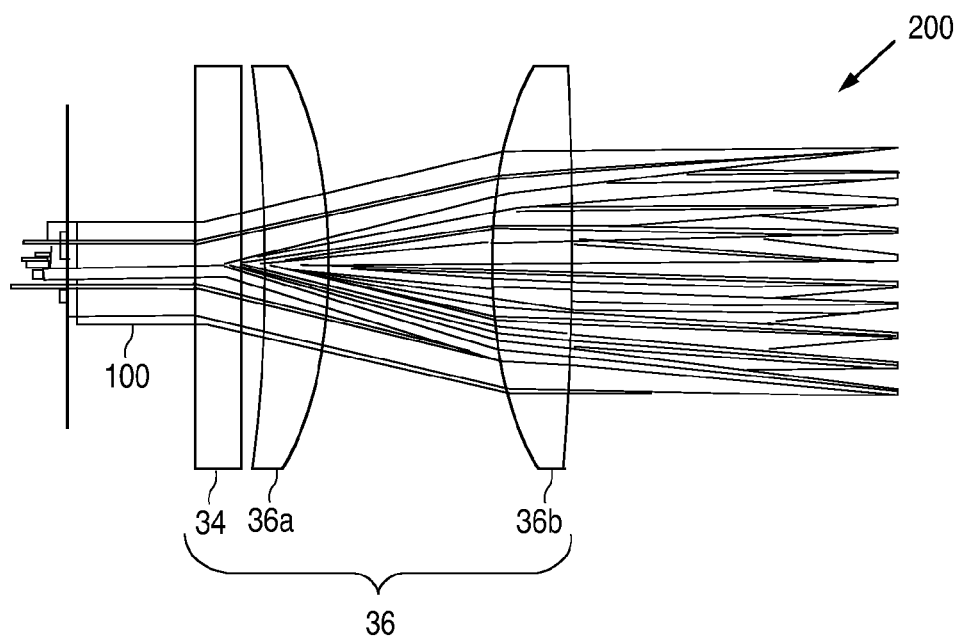
FIGS. 3A-3C are side elevation views of the diffractive element and optics from the system of FIGS. 2A and 2B, schematically illustrating splitting of the beam into subbeam, and focusing of the sub-beams by the optics.

Diffractive element 34 splits the scanned beams into a fixed number (e.g. 6, 8, or 10) of sub-beams 200 having fixed angles between them (FIG. 3). The diffractive element may be manufactured in a number of ways to optimize uniformity of the sub-beams. For example, the diffractive element may be one that eliminates the effect of the zero order and/or that skips the even orders to maintain symmetry around the zero order. Off-axis diffractive elements may also be used. Suitable diffractive elements are manufactured by MEMS Optical of Huntsville, Ala.

Optics 36 focus the sub-beams 200 to a predetermined spot size onto the tissue to be treated. In the illustrated embodiment, optics 36 includes a meniscus lens 36a and—a double convex lens 36b, each of which is made of sapphire. See also FIGS. 3A-3C.

The separation distance between the spots impinged onto the target tissue is determined by the focal length of the optics 36 and the angles of the sub-beams 200 formed by the diffractive element. The arrangement of the optics 36 also determines the working distance (defined as the distance between the tissue surface and the output of the optics 36).

Figure 3B:
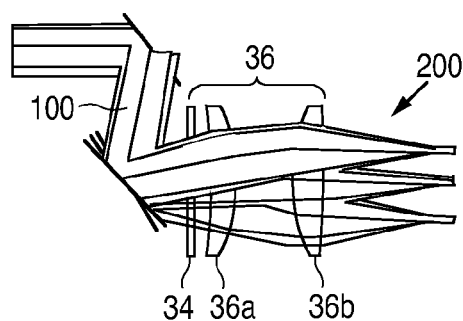

For example, in one embodiment illustrated in FIG. 3B, the lenses 36a, 36b are designed to impinge 300µ diameter spots onto the tissue surface, with a 20 mm working distance, and a 1.3 mm depth of focus. This arrangement gives a 0.44 mm spot offset/degree beam angle, meaning that if the diffractive element gives angles of 1 degree between each beam, the center-to-center separation distance between the spots will be 0.44 mm.

Figure 3C:
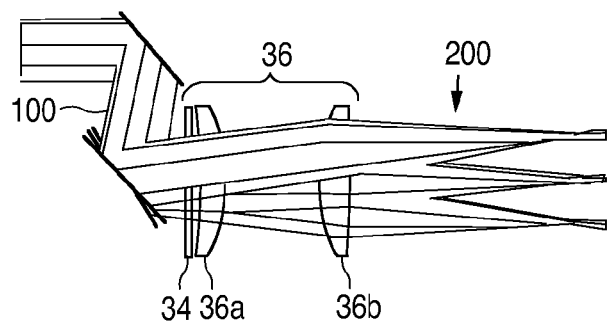

In contrast, FIG. 3C illustrates another design of lenses 36a, 36b which create 300µ diameter spots with a 41 mm working distance, a 3 mm depth of focus, and a 0.84 mm spot offset/degree beam angle.

Referring again to FIGS. 2A and 2B, the handpiece additionally includes an aiming diode 38 positioned to generate a visible aiming beam of light that is combined with the laser output beam 100. The aiming beam is likewise diffracted into sub-beam so that the aiming sub-beams are parallel and coincident with the treatment sub-beams.

In a preferred mode of operation, the scanning minors scan the pulsed output beam across the diffractive element. As a result, the sub-beams 200 generated by the diffractive element form a matrix of small diameter (e.g. approximately 200-400µ) treatment spots on a treatment area of the skin. Treatment spots may have a depth of approximately 200µ to 1 mm, and the energy per pulse of each treatment sub-beam is approximately 30-150 mJ. An optimal treatment speed is approximately 1 cm$^2$/sec.

The stepper motors may be operated in a number of treatment modes to produce spot matrices having a variety of spot densities. Three exemplary modes will be described with reference to FIGS. 4A-4C, which illustrate three examples of treatment patterns that can be produced using the disclosed laser. Each of the illustrated treatment patterns represents a pattern generated in a 14 mm by 18 mm treatment area using a diffractive element that yields eight treatment sub-beams.

Figure 4A:
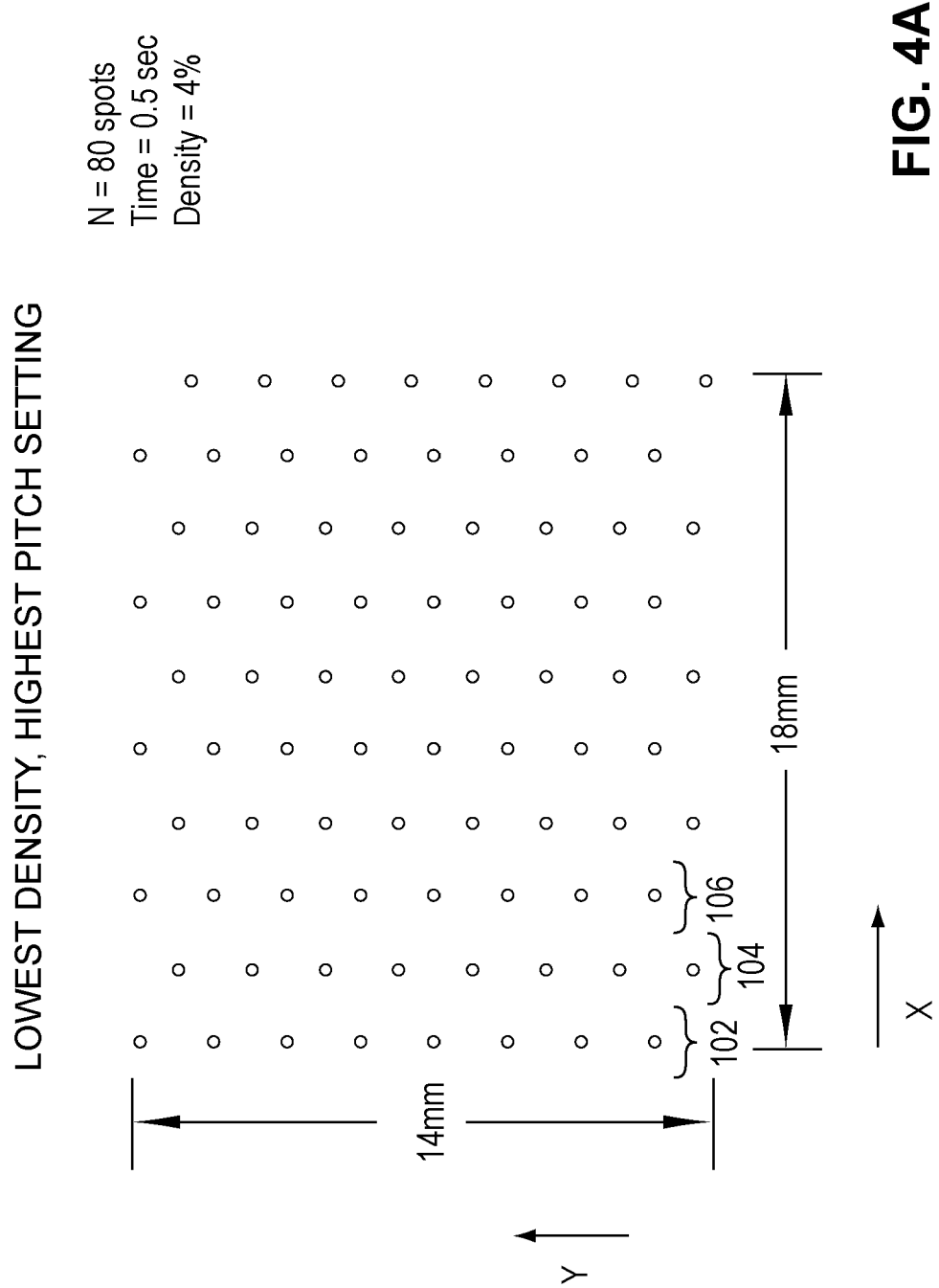
FIGS. 4A through 4C illustrate three examples of spot patterns that can be generated using the disclosed handpiece.

In FIG. 4A, treatment begins with the formation of column 102 of treatment spots when the eight sub-beams are in their initial position. Scanning motors 32a, 32b are energized between laser pulses to step the mirrors 30a, 30b, causing a shift in the sub-beam orientations. Activation of the scanning motors causes one of the scanning minors to shift the orientation of the sub-beams along the X-axis, and causes the other one of the scanning minors to shift the orientation of the sub-beams downwardly along the Y-axis, forming column 104 of treatment spots. The minors are again scanned, this time to move the sub-beams to the right along the X-axis and upwardly along the Y-axis, so that the next pulse of energy from the laser 18 generates column 106 of treatment spots. The process is repeated (toggling the array of spots up and down) to produce multiple columns of treatment spots. FIG. 4A shows a matrix of 80 treatment spots with a spot density of approximately 4%. The system is capable of forming the matrix in less than 1 second, and preferably approximately 0.5 sec.

Figure 4B:
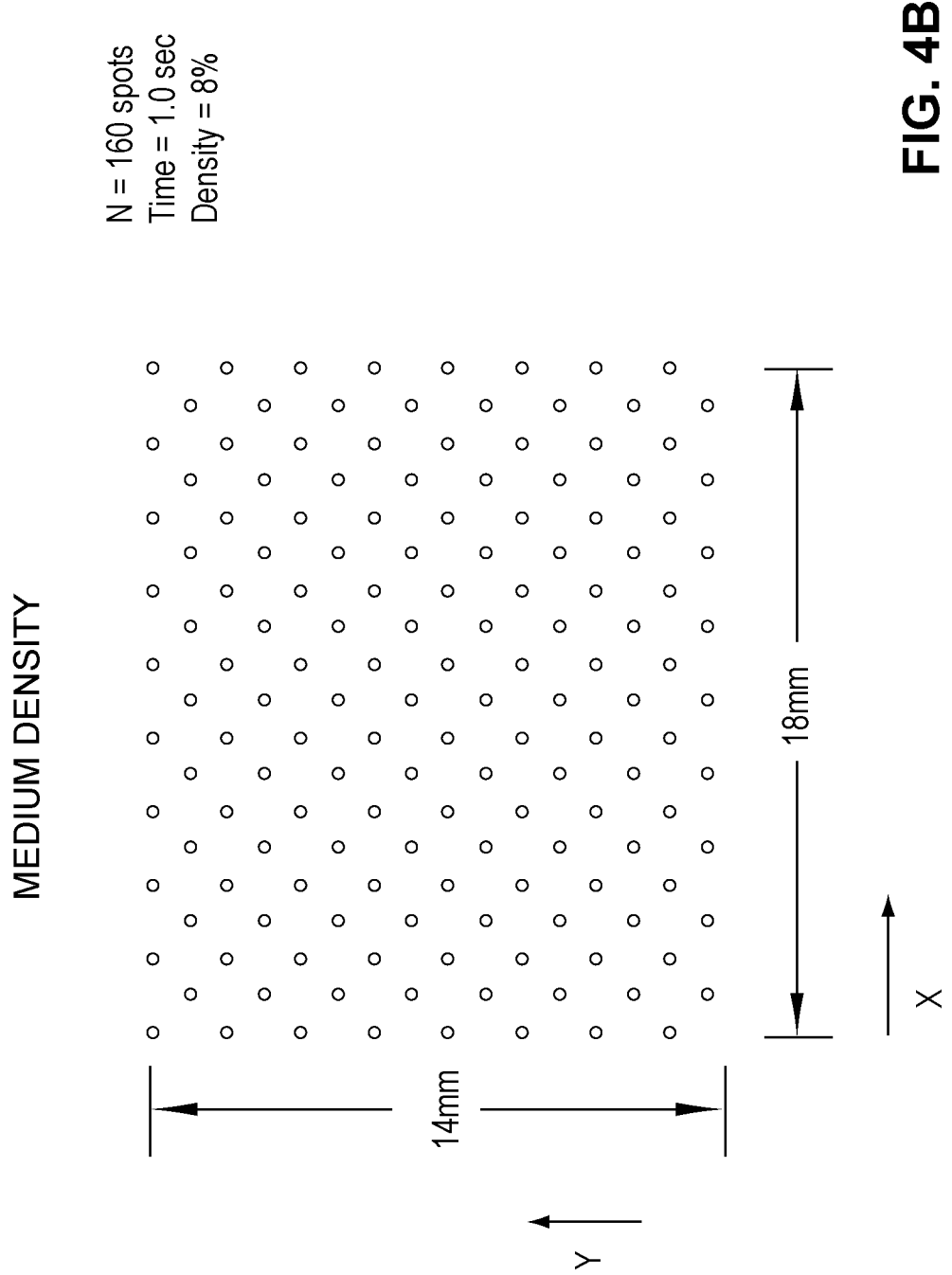

The FIG. 4B treatment pattern may be formed using a mode similar to that described with respect to FIG. 4A, but by shortening the X-direction scanning distance by half to form a denser spot array. Here, a matrix of 160 treatment spots with a spot density of approximately 8% is shown. In one embodiment, the treatment time to form this matrix of spots may be approximately one second.

Figure 4C:
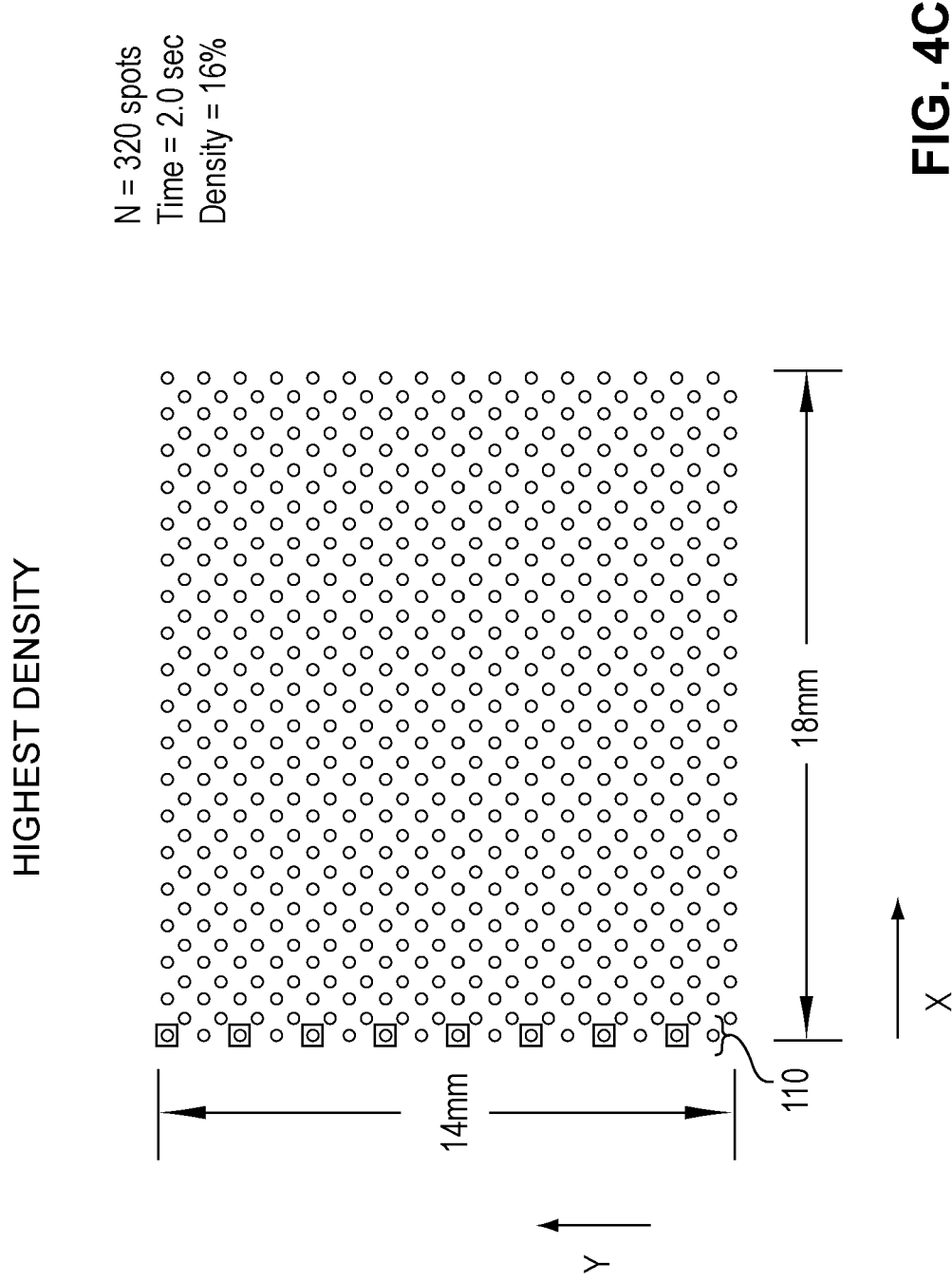

In the treatment pattern shown in FIG. 4C, the spot density is further increased to 16%. As shown, although the diffractive element produces eight sub-beams, each column includes sixteen treatment spots. In column 110, boxes are drawn around alternate spots to identify the initial eight treatment spots. The Y-axis stepper motor is then activated between treatment pulses to reorient the eight treatment sub-beams to form additional spots between the initial eight treatment spots. The X-axis stepper motor is then used to orient the sub-beams to form additional treatment columns. As with the FIGS. 4A and 4B patterns, the pattern is created by repeatedly stepping the X-axis and Y-axis motors to re-orient the eight treatment sub-beams. The sequence of the X-axis and Y-axis shifts needed to complete the pattern is not critical, but is generally optimized to minimize the treatment time, which in this mode is ideally about 2 sec or less for the entire matrix.

In use, the operator would select the desired spot density through the user interface 13 on the console 14. Based on this input, the controller 19 sends signals to the flashlamp to generate the laser pulses and coordinates the pulsed operation with the movement of the scanning minors 30a and 30b. Some additional details of control circuitry suitable for implementing the design is set forth in U.S. Publication 2007/026504 with particular reference to FIG. 3.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

We claim:

1. A device for scanning a pulsed beam of laser radiation generated by a laser onto tissue comprising:

optics for focusing the beam onto the tissue wherein the optics include a diffractive optical element for splitting the beam into at least three spaced apart sub-beams and a lens assembly adjacent and closely spaced to the diffractive optical element without any beam steering elements therebetween, said lens system for directing the beams along separate paths and for focusing the sub-beams onto tissue in a linear array of spots; and a reflective scanner receiving the beam generated by the laser, said scanner for varying the entry angle of the beam and for translating the beam to different positions on the diffractive optical element to cause the sub-beams to be directed to different locations on the tissue.

2. The device of claim 1 wherein the scanner is operative to move the beam in two mutually perpendicular axes so that the density of the spots on the tissue can be controlled in two axes.

3. The device of claim 2 wherein between laser pulses, the scanner is repositioned so that the next array of spots on the tissue will be shifted in both axes compared to the previous array of spots on the tissue.

4. The device of claim 2 wherein said scanner includes a pair of mirrors mounted on stepper motors.

5. The device of claim 1 wherein said diffractive optical element splits the beam into at least six spaced apart sub-beams.

6. A device for scanning a beam of laser radiation onto tissue comprising:
- a laser generating a beam of radiation;
- a diffractive optical element for splitting the laser beam into a linear array of at least three sub-beams;
- a scanner positioned between the laser and the diffractive optical element for varying the entry angle and position of the beam axis onto the diffractive optical element;
- a lens system adjacent and closely spaced to the diffractive optical element without any beam steering elements therebetween, said lens system for focusing the sub-beams onto the tissue to create a linear array of substantially equally spaced treatment spots; and
- a controller operatively connected to the laser and the scanner and responsive to user input to create a two dimensional scanned pattern of spots and wherein in operation, the laser is commanded to deliver a first pulse which creates a line array of spots on the tissue, whereupon the controller causes the scanner to translate the beam axis to a second position on the diffractive optical element and thereafter the laser is commanded to deliver a second pulse which creates a line array of spots spatially separate from the first line array of spots, and wherein the controller is configured to successively translate the beam axis to a third and subsequent positions on the diffractive optical element while generating additional laser pulses at each said position to create a two dimensional array of spots on the tissue and wherein the spacing between the positions on the diffractive optical element can be controlled to control the density of the spots on the tissue.

7. The device of claim 6, wherein the scanner is operative to move the beam in two mutually perpendicular axes so that the density of the spots on the tissue can be controlled in two axes.

8. The device of claim 7 wherein between laser pulses, the scanner is repositioned so that the next array of spots on the tissue will be shifted in both axes compared to the previous array of spots on the tissue.

9. The device of claim 7 wherein the scanner operates to adjust the beam axis on the diffractive optical element so that the array of spots on the tissue is:
   (a) moved in both a first and second axes in a first direction on the tissue; and
   (b) then moved in the first axis in the first direction and the second axis in a direction opposite the first direction and wherein the steps (a) and (b) are repeated to create a two dimensional array of spots.

10. The device of claim 7 wherein said scanner includes a pair of mirrors mounted on stepper motors.

11. The device of claim 7 wherein said diffractive optical element splits the beam into at least six spaced apart sub-beams.

* * * * *